US006629944B2

(12) United States Patent
Smart (10) Patent No.: US 6,629,944 B2
(45) Date of Patent: Oct. 7, 2003

(54) LIMB-POSITIONING AND TRACTION DEVICE

(76) Inventor: Kenneth Thomas Smart, 233 Carlaw Ave., Suite 401, Toronto, Ontario (CA), M4M 3N6

( * ) Notice: Subject to any disclaimer, the term of this patent is extended or adjusted under 35 U.S.C. 154(b) by 272 days.

(21) Appl. No.: 09/799,343

(22) Filed: Mar. 6, 2001

(65) Prior Publication Data

US 2002/0128577 A1 Sep. 12, 2002

(51) Int. Cl.[7] .................................................. A61F 5/00
(52) U.S. Cl. .............................. 602/36; 128/845; 5/624
(58) Field of Search ................................. 128/845, 846, 128/878; 5/624, 623, 648, 650, 658, 651; 602/62, 63

(56) References Cited

U.S. PATENT DOCUMENTS

| | | | |
|---|---|---|---|
| 4,431,329 A | | 2/1984 | Baitella |
| 4,579,324 A | | 4/1986 | McConnell |
| 4,702,465 A | | 10/1987 | McConnell |
| 4,858,903 A | * | 8/1989 | Tari ............................ 269/328 |
| 5,582,379 A | * | 12/1996 | Keselman ....................... 5/621 |
| 5,775,334 A | * | 7/1998 | Lamb .......................... 128/845 |
| 5,918,330 A | * | 7/1999 | Navarro ......................... 5/651 |
| 5,961,085 A | * | 10/1999 | Navarro ......................... 5/624 |
| 5,961,512 A | | 10/1999 | Purnell |

* cited by examiner

Primary Examiner—Michael A. Brown
(74) Attorney, Agent, or Firm—Nancy E. Hill; Hill & Schumacher (57) ABSTRACT

A limb-positioning device is adapted for use in an operating room and is attachable to an operating room table. The limb-positioning device includes a full motion arm, a patient-receiving surgical device and a tension controller. The full motion arm has a plurality of pivotally connected arms with a plurality of joints therebetween. One end of the full motion arm is adapted to be attached to an operating room table. The patient-receiving surgical device is attached to a block joint at the distal end of the full motion arm. There is a tension controller for each joint. Preferably the tension controller concurrently controls the tension in each joint. The patient-receiving surgical device may be a forearm tray, a lower leg tray, a distraction harness or a Chinese finger trap assembly. There is provided a method of using the limb-positioning device. In addition, a patient-receiving surgical device includes a patient-receiving portion and a bar attached thereto. The bar is attachable to a receiving channel on an attachment block that is attached to a ball joint at the distal end of a full motion arm of a limb-positioning device.

22 Claims, 9 Drawing Sheets

LIMB-POSITIONING AND TRACTION DEVICE

FIELD OF THE INVENTION

This invention relates to limb-positioning and traction devices and in particular limb-positioning and traction devices that can be adapted for use for a variety of surgical procedures, a variety of positions and a variety of limbs.

BACKGROUND OF THE INVENTION

In the performance of surgery or other medical procedures it is often desirable to support a limb or other part of the patient's body in a particular position during the procedure. Since no two patients' bodies are alike, it is important that a device which facilitates such positioning can accommodate a diverse group of patient sizes. The positioning of the limb is of particular importance during orthopaedic surgery, particularly with regard to arthroscopic surgery wherein the patient's joint is manipulated to provide access to the arthroscope.

To date some limb-positioning devices have been suggested. However, typically these devices are large devices that are difficult to use and often they are single purpose or essentially single purpose devices. One such device is shown in U.S. Pat. Nos. 4,579,324 and 4,702,465 both issued to McConnell on Apr. 1, 1986 and Oct. 27, 1987. This device is for use in an operating room for positioning a limb. It is a large unwieldy device that would be difficult to store and more difficult to sterilize. Further, there are a number of different adjustments that need to be made to secure the device. Thus it would be difficult to easily adjust the position of the limb. Further it would be difficult for one person to adjust the position on their own. Accordingly, it is not widely used in operating rooms. Another device is shown in U.S. Pat. No. 5,961,512 issued to Purnell on Oct. 5, 1999. This is a single purpose device for positioning an arm during shoulder surgery. Similarly this device is large, difficult to store and more difficult to sterilize. In addition, as with the above device there are a number of adjustments that must be made to position the limb. Thus a number of adjustments need to be made to move the limb.

Accordingly, it would be advantageous to provide a device that is easy to store, easy to sterilize and can be used for a number of different procedures.

SUMMARY OF THE INVENTION

The present invention is a limb-positioning device that is adapted for use in an operating room and is attachable to an operating room table. The limb-positioning device includes a full motion arm, a patient-receiving surgical device and tension controller. The full motion arm has a plurality of pivotally connected arms with a plurality of joints therebetween. One end of the full motion arm is adapted to be attached to an operating room table. The patient-receiving surgical device is attached to a block joint at the distal end of the full motion arm. There is a tension controller for each joint. Preferably the tension controller concurrently controls the tension in each joint. The patient-receiving surgical device may be a forearm tray, a lower leg tray, a distraction harness or a Chinese finger trap assembly.

In another aspect of the invention there is provided a method of using the limb-positioning device. The method for positioning a portion of a patient's anatomy includes the steps of providing a limb-positioning device; attaching the limb-positioning device to an operating room table; adjusting the tension controller; supporting the portion of the patient's anatomy on the patient-receiving surgical device; positioning the patient-receiving surgical device; and tightening the tension controller. The limb-positioning device includes a full motion arm having a plurality of pivotally connected arms with a plurality of joints therebetween and one end of the full motion arm being adapted to be attached to an operating room table; a patient-receiving surgical device attached to a block joint at the distal end of the full motion arm; and a tension controller for controlling the tension of each joint.

In a further aspect of the invention, a patient-receiving surgical device includes a patient-receiving portion and a bar attached thereto. The bar is attachable to a receiving channel on an attachment block that is attached to a ball joint at the distal end of a full motion arm of a limb-positioning device. The patient-receiving portion may be a forearm tray, a lower leg tray, a distraction harness or a Chinese finger trap assembly.

The limb-positioning described herein is relatively easy to store and sterilize. It has a single fixation point and a plurality of joints with variable friction level so that a surgeon can position patient limb without the aid of an assistant. Once positioned the device can be secured in that position. The device can accommodate limbs of varying weight. The device is designed so that if it is draped in a disposable drape and used with a disposable patient-receiving device no large part need be placed in the autoclave. This reduces the cool down tines and lowers device inventory requirements since units need not be cycled through infection control. The device herein is adapted to be used with different patient-receiving surgical devices whereby the device can be used for shoulder, knee, ankle, elbow, hip and wrist surgery.

Further features of the invention will be described or will become apparent in the course of the following detailed description.

BRIEF DESCRIPTION OF THE DRAWINGS

The invention will now be described by way of example only, with reference to the accompanying drawings, in which.

DETAILED DESCRIPTION OF THE INVENTION

Figure 1:
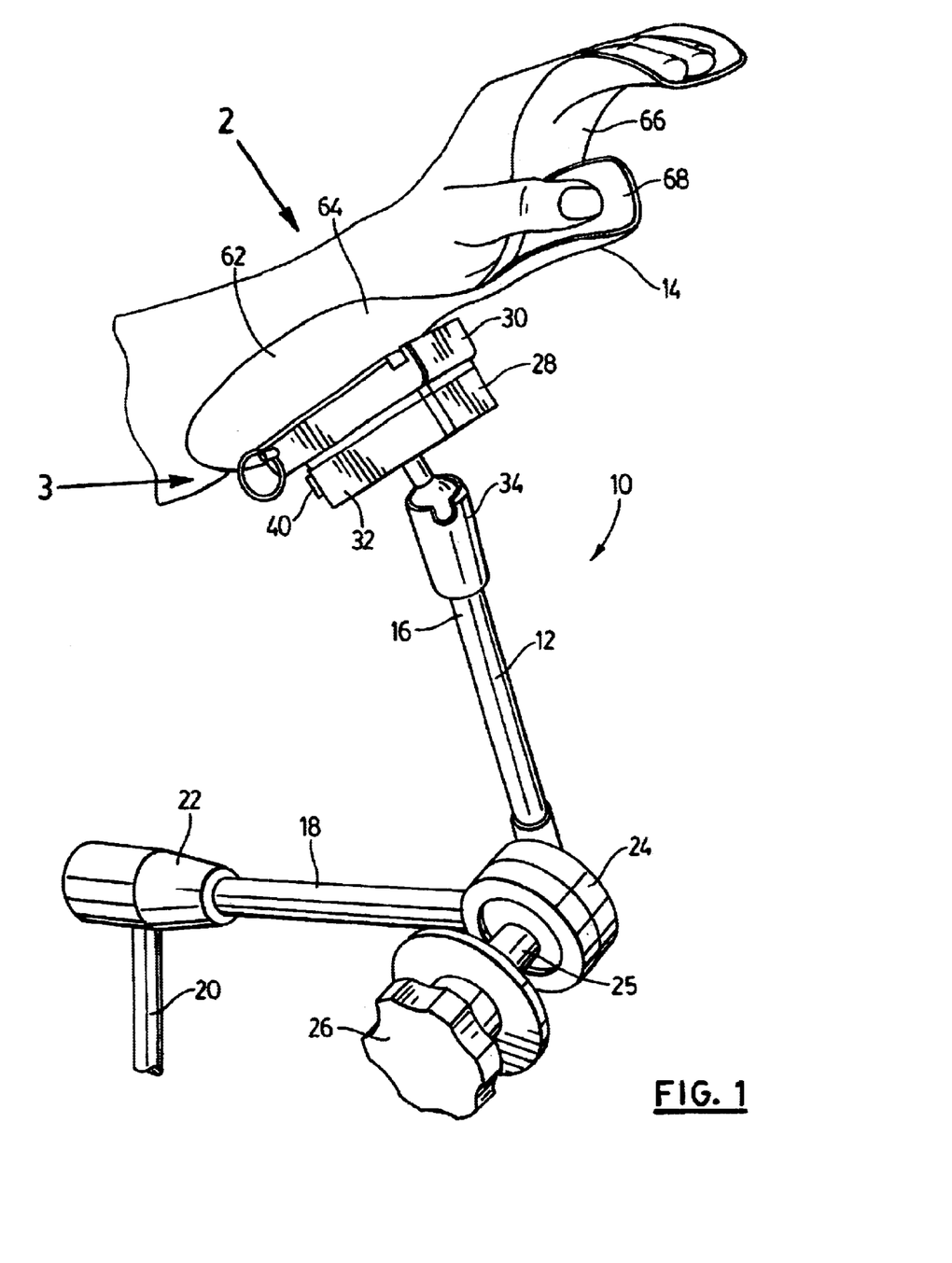
FIG. 1 is a perspective view of a forearm tray embodiment of the limb-positioning and traction device constructed in accordance with the present invention.

Referring to FIG. 1, a limb-positioning device is shown generally at 10. The limb-positioning device includes a full motion arm 12 and a patient-receiving surgical device 14.

The full motion arm 12 is a stainless steel device with three points of motion that are locked and unlocked by a centrally located tensioning knob. The full motion arm 12 includes a distal arm 16, a connection arm 18 and an attachment arm 20. Preferably the attachment arm 20 is a Clark post. The Clark post is a solid metal rod that allows the device to be attached to a standard operating room table via a Clark attachment, Between each pair of arms 16, 18 and 20 there is a joint which allows movement of one arm relative to the other. Between attachment arm 20 and connection arm 18 there is an attachment ball joint 22. Between the connection arm 18 and the distal arm 16 there is a central joint 24 that has one degree of freedom and the arms can rotate 360 degrees. A post 25 extends outwardly from the central joint 24 and a tension adjustment knob 26 is removably attached to the post 25.

Figure 3:
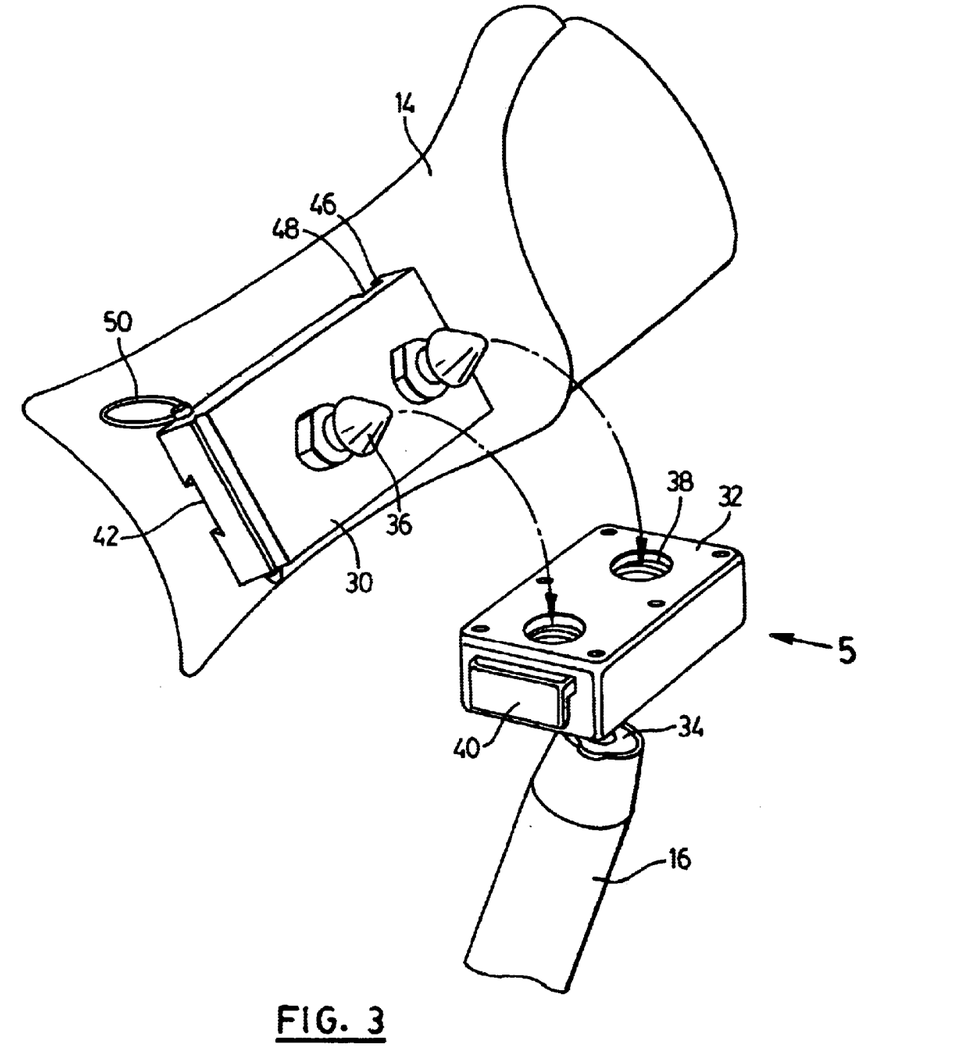
FIG. 3 is a perspective blown apart view of the coupling potion of the limb-positioning and traction device showing the detachable forearm tray detached from the female portion of the block.
Figure 5:
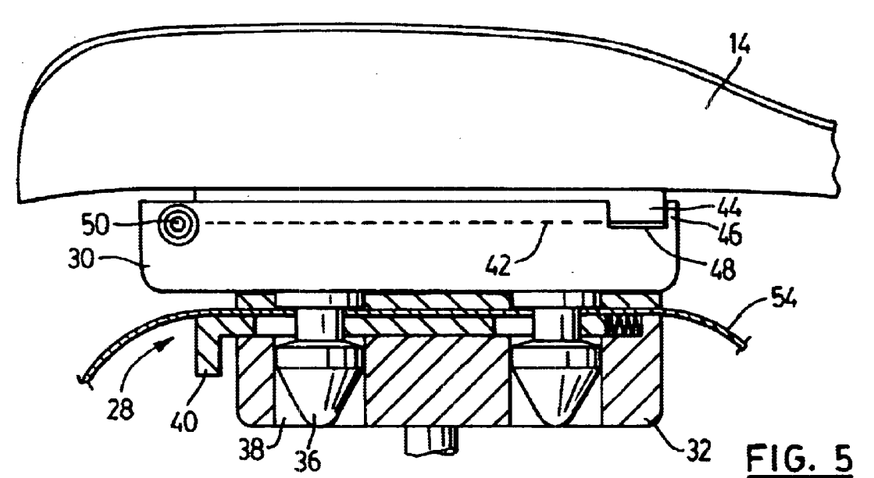
FIG. 5 is a sectional view of the attachment portion of the limb-positioning and traction device including a drape showing the detachable forearm tray attached to the block.
Figure 6:
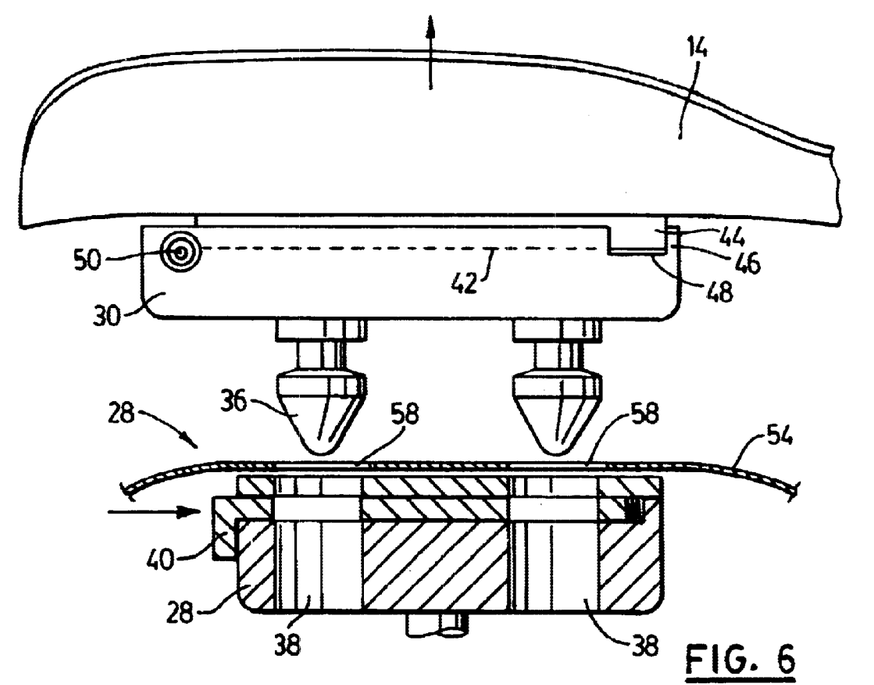
FIG. 6 is a sectional view of the attachment portion of the limb-positioning and traction including a drape device similar to that shown in FIG. 5 but showing the detachable forearm tray detached from the mount.
Figure 7:
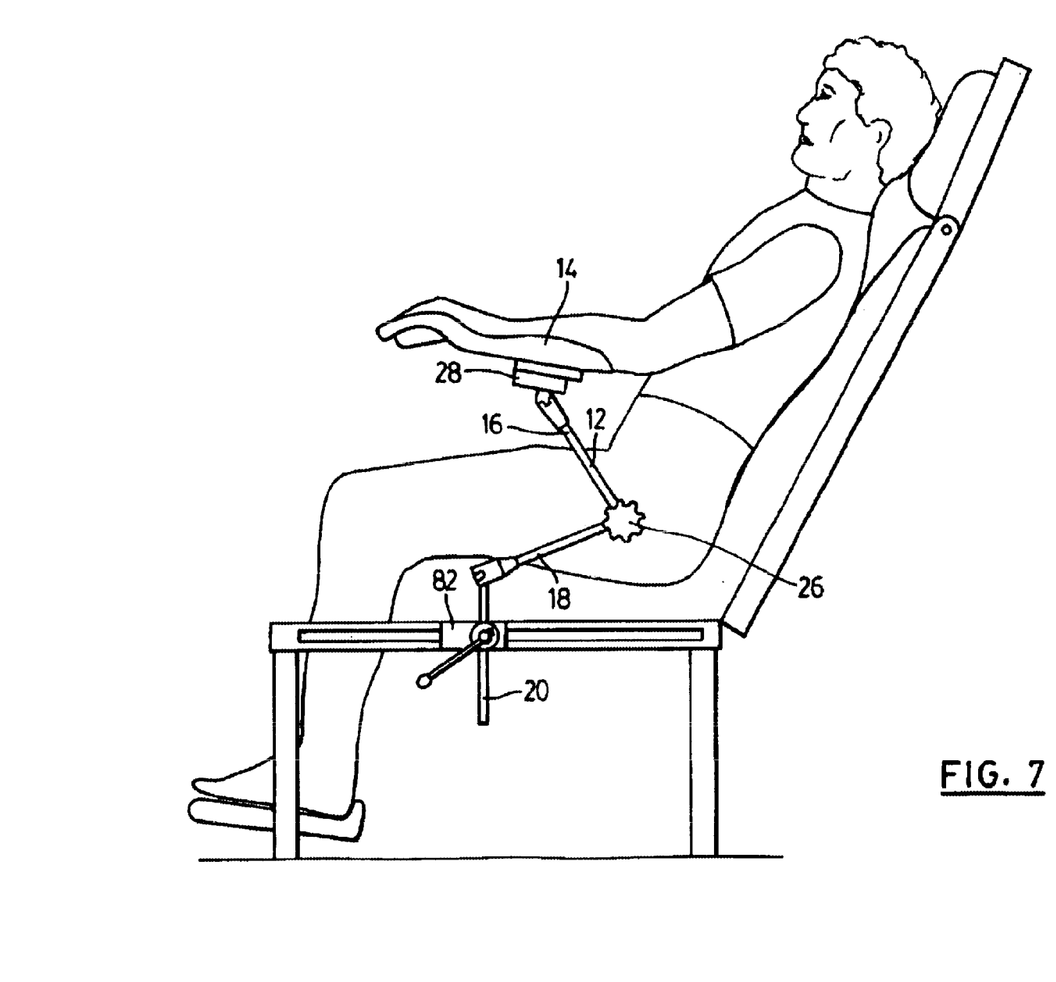
FIG. 7 is a side view of the limb-positioning and traction device attached to an operating table in a beach chair configuration.

Preferably the surgical device 14 is releasably attachable to the motion arm 12. An attachment block 28 is used as the interface between the patient-receiving surgical device 14 and the motion arm 12. Attachment block 28 has a male portion 30 and a female portion 32. Female portion 32 is attached to the motion arm 12 with a block ball joint 34. A pair of pins 36 (as best seen in FIGS. 3, 5 and 6) extend outwardly from the male portion 30 and are received into a corresponding pair of apertures 38 in female portion 32. A spring loaded tension clip 40 holds the pins 36 in place.

Figure 2:
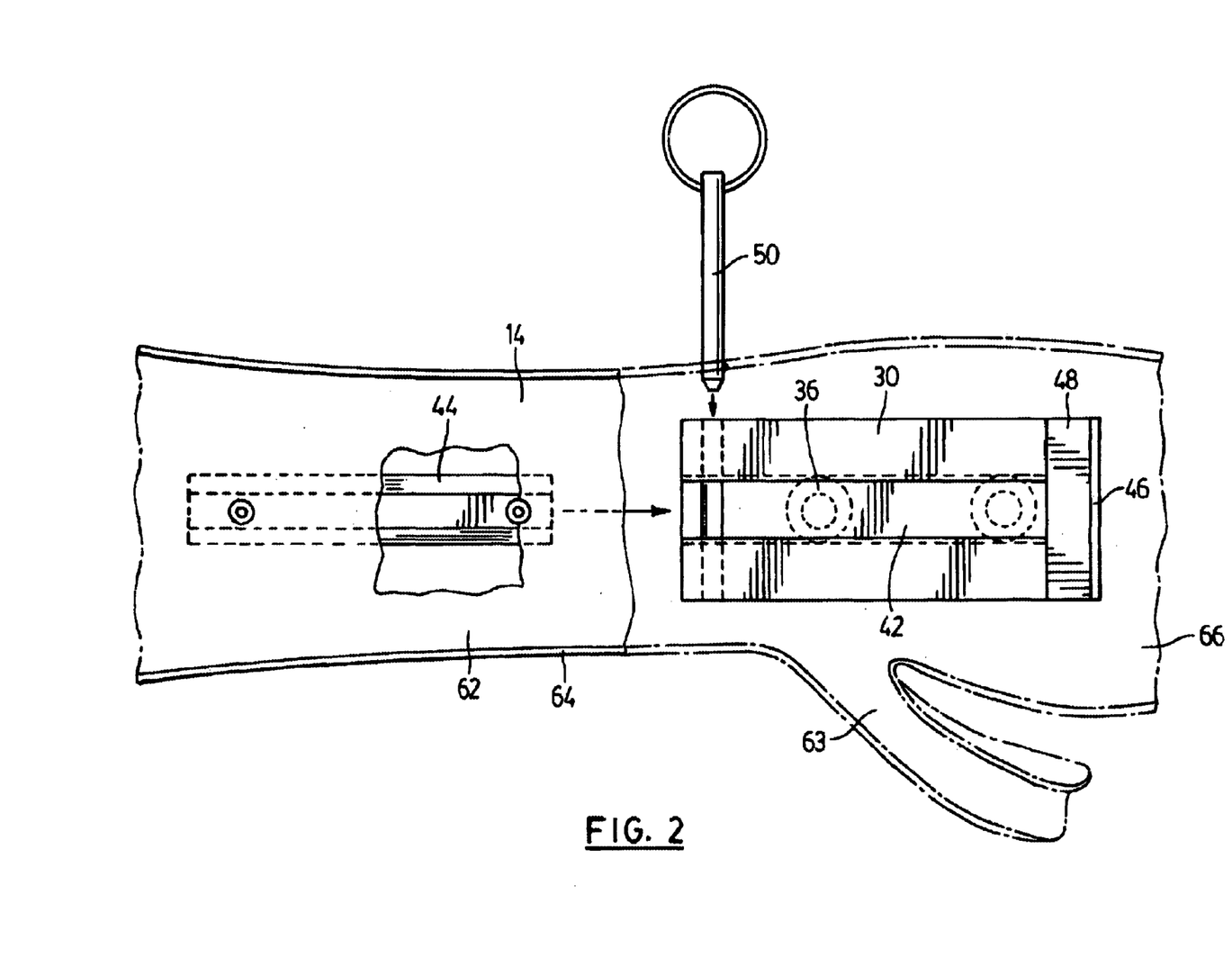
FIG. 2 is an enlarged cut-away top view of the detachable forearm tray as viewed in the direction of arrow 2 in FIG. 1.

Preferably surgical device 14 is releasably attachable to the male portion 30 of the attachment block 28. A receiving channel 42 is formed in the male portion 30 of the attachment block 28 on the opposed side from the pins 36, as best seen in FIG. 2. A bar 44 is attached to the surgical device 14. The bar 44 has a trapezoidal shaped cross section that slides into the channel 42. Channel 42 has an end stop 46 and a lateral channel 48. Lateral channel 48 facilitates easy cleaning of the male portion 30. A mount pin 50 holds the bar 44 in place. The male portion 30 of the attaching block 28 and the bar 44 together provide a sterile interface between the female portion 32 of the attaching block 28 and the patient-receiving surgical device 14.

Preferably the tension adjustment knob 26 is a round, detachable knob that provides a sterile interface with which the surgeon can adjust the tension and holding strength of the motion arm 12 during the surgical procedure. The motion arm 12 is constructed such that adjusting knob 26 controls the tension and hold strength of attachment ball joint 22, the central joint 24 and the block ball joint 34. An example of a full motion arm that is adaptable to this application is shown in U.S. Pat. No. 4,431,329 issued to Baitella on Feb. 14, 1984.

Figure 4:
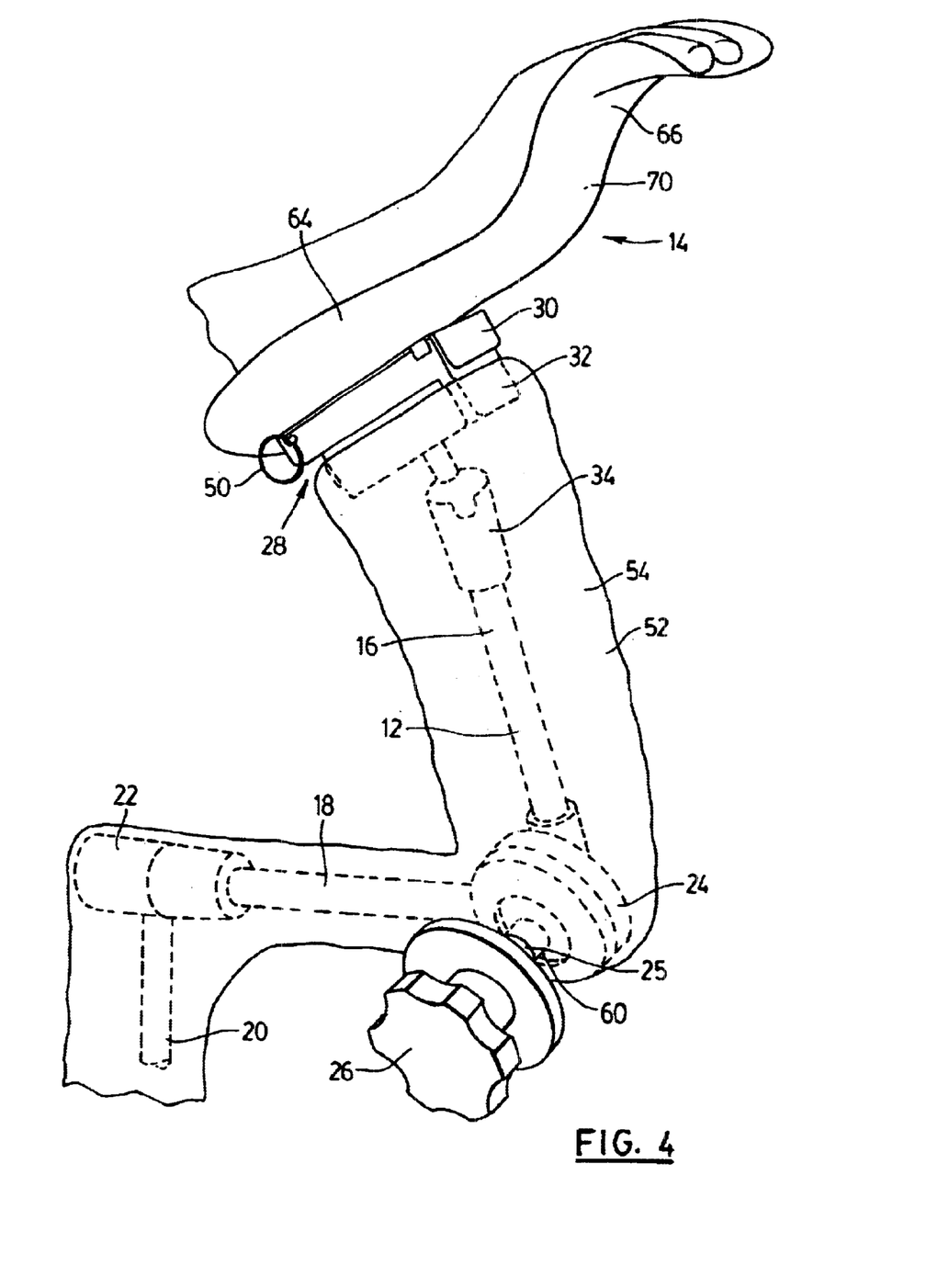
FIG. 4 is a perspective view of the limb-positioning and traction device showing an alternate embodiment of the forearm tray and showing a drape over the full motion arm.

To use the limb-positioning and traction device 10 shown herein in surgery it needs to be either autoclaved or draped, in accordance with today's standards. Accordingly, if the limb-positioning and traction device 10 is to be autoclaved it must be made of the appropriate materials. Alternatively, if it is to be draped an appropriate drape 52 is shown in FIGS. 4 to 6. The drape 52 includes a sleeve drape 54 and a skirt drape (not shown). Typically these drapes are disposable. The sleeve drape 54 has a pair of burst points 58 that correspond to apertures 38 in female portion 32 of attachment block 28 and a fenestration 60 that is positioned such that post 25 extends therethrough. Accordingly, in use the sleeve drape 54 is pulled over the full motion arm 12 and the burst points 58 and fenestration 60 are positioned as described above. A sterile or autoclaved tension adjustment knob 26 is then attached to the post 25 of central joint 24. Similarly the sterile surgical device 14 will be attached to sterile or autoclaved male portion 30 of attachment block 28. The skirt drape slides over the draped motion arm and the Clark attachment to provide a sterile barrier between unautoclaved of limb-positioning and traction device 10 and the surgical field.

Preferably patient-receiving surgical device 14 is a disposable device. A wide variety of different devices could be attached to the motion arm 12. A few such different devices are shown in the drawings herein. A forearm tray 62 is shown in FIGS. 1 and 2 wherein the tray is shaped to receive the forearm. The forearm tray 62 includes a forearm portion 64, a hand portion 66 and a thumb portion 68. The side of the tray 62 is cut away such that the patient's wrist bone will not touch the tray. An alternate forearm tray 70 is shown in FIG. 4 wherein the tray has a forearm portion 64 and a hand portion 66 but no thumb portion. Typically once the forearm is positioned in the forearm tray 70 the forearm will be secured in place with surgical tape such as Koban™ tape.

Figure 8:
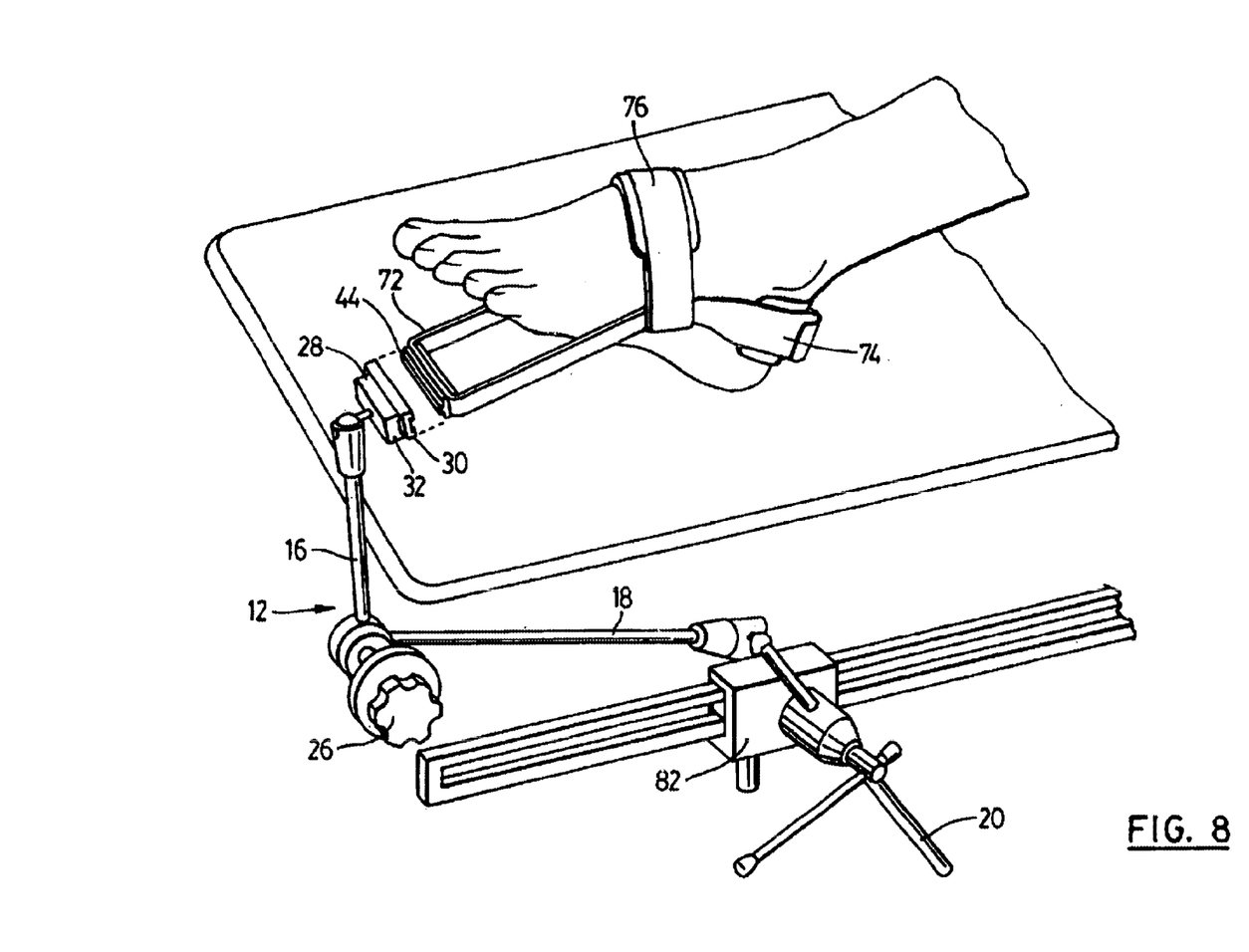
FIG. 8 is a perspective view of a distraction harness embodiment of the limb-positioning and traction device constructed in accordance with the present invention.

Referring to FIG. 8 a distraction harness or ankle strap 72 is shown attached to bar 44. Ankle strap 72 includes a heel strap 74 and an arch strap 76. It will be appreciated by those skilled in the art that the full motion arm 12 can be manipulated such that tension is exerted on the ankle.

Figure 9:
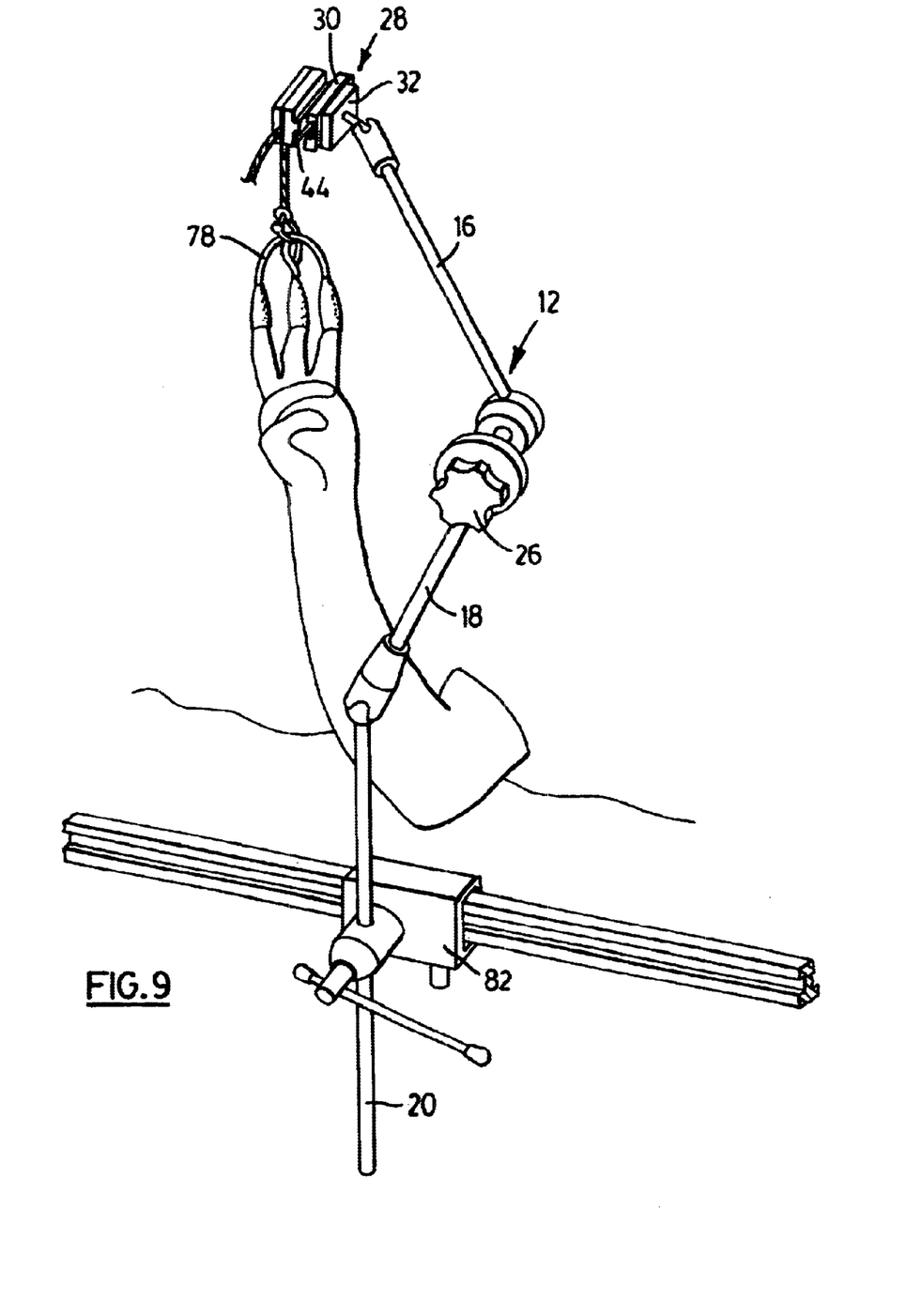
FIG. 9 is a perspective view of a Chinese finger trap assembly embodiment of the limb-positioning and traction device constructed in accordance with the present invention.

Referring to FIG. 9 a plurality of Chinese finger trap assembly 78 are shown attached to bar 44. Similar to the ankle embodiment, the full motion arm 12 can be manipulated such that upward tension is exerted on the arm. Note that an upper arm retention strap will likely also be used during wrist surgery.

Figure 10:
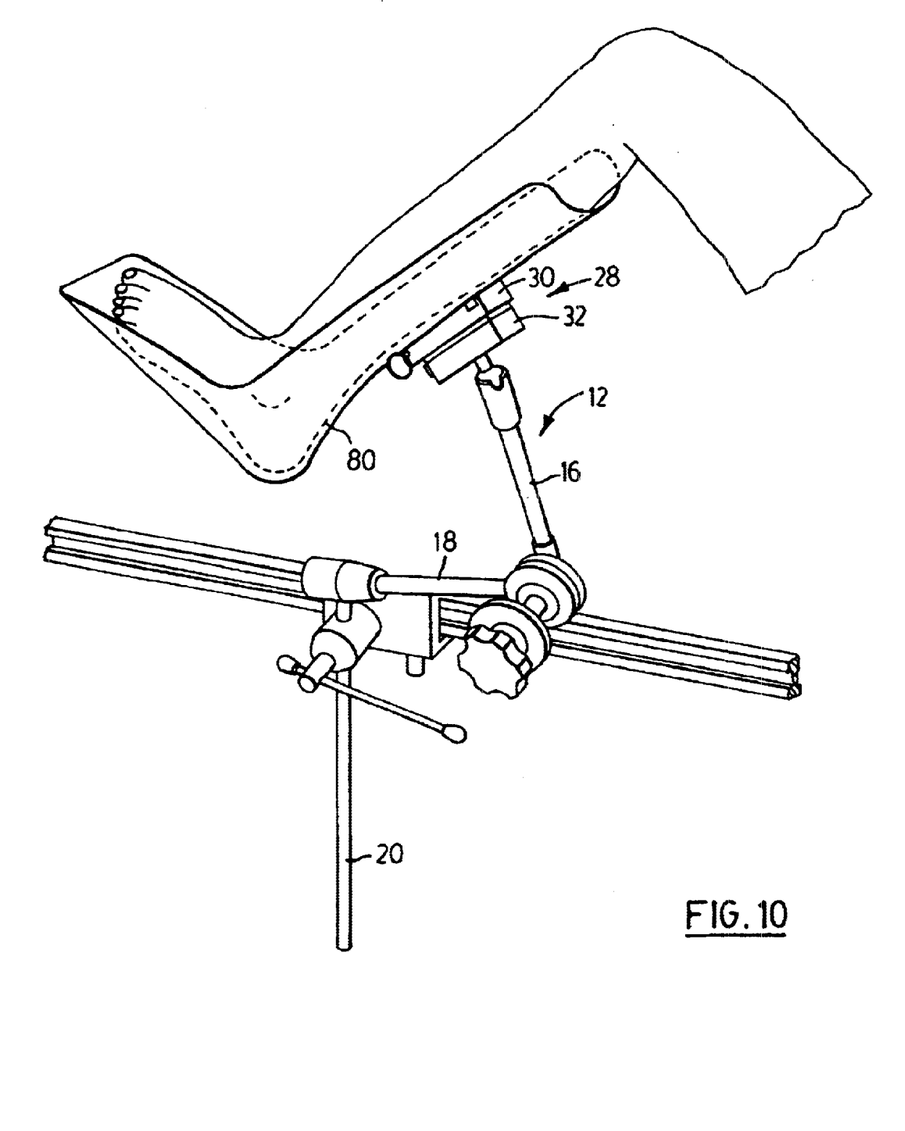
FIG. 10 is a perspective view of a lower leg tray embodiment of the limb-positioning and traction device constructed in accordance with the present invention.

Referring to FIG. 10 a lower leg tray 80 is shown attached to bar 44. It will be appreciated by those skilled in the art that once the patient's leg is secured in the tray. As with the forearm, the patient leg is typically secured in place with surgical tape. The full motion arm 12 may be manipulated to achieve flexion, extension, varus, vulgus, abduction and adduction. This is of particular importance when conducting orthopaedic surgery. In addition, the ease of manipulating the lower limb will also be advantageous when conducting gynecological procedures.

Alternatively, the patient-receiving surgical devices 14 described above may be autoclavable. This may be of particular importance in jurisdictions where there are severe limitations on the amount and composition of materials that may be included in the garbage.

In use after the patient has been positioned on the operating table, the full motion arm 12 is attached in the desired position by sliding the Clark post or attachment arm 20 into the rail clamp 82 and tightening the clamp. Before or after the affected limb has been prepped, the motion arm 12 is locked in a vertical position and the drape 52 is arranged over the motion arm 12. The sterile sleeve drape 54 is slid over the motion arm 12. The burst points 58 are positioned over apertures 38 in the female portion 32 of the attachment block 28 The fenestration 60 is positioned over the post 25 extending outwardly from the central joint 24. The sterile skirt drape is then pulled over the draped arm and the wings are extended to cover the patient. The sterile adjustment knob 26 is pushed onto the post 25 through a fenestration 60 in the side of the sleeve drape 54. The male portion 30 of the attachment block 28 is fastened to the female portion 32 by pushing the pins 36 through the sleeve drape 54 into the tension clip 40 in the female portion 32. The appropriate patient-receiving surgical device 14 is attached to the attachment block 28 by sliding the bar 44 into the receiving channel 42 and locking it in place with mount pin 50. Where appropriate the patient's limb is secured to the patient-receiving device 14. To loosen the device for positioning, the tension adjustment knob 26 is rotated counterclockwise until the necessary motion is obtained. Then device 10 is positioned into the desired position by rotating the tensioning knob clockwise. A mid-point adjustment will allow the limb to be moved into any position under tension and maintain that position until the tension can be locked. There is a wide variety of tension options available to the user. For example the device can be positioned in the general area with minimal tension. Thereafter the finer positioning can be done at a much higher tension. Further, it will be appreciated by those skilled in the art that if the position of the limb need be moved during surgery, the knob can easily be loosened, the limb moved and the knob resecured. Alternatively the mount pin 50 can be easily removed and the surgical device 14 can be removed from the positioning device 10 and then the surgical device 14 can be reattached so that the limb is back to the same position.

It will be appreciated by those skilled in the art that there are a number of advantages that can be achieved, particularly in an operating room, by using the limb-positioning device 10 described herein. Most importantly the limb-positioning device is easy to use. It is attachable to a standard Clark rail clamp commonly used in operating rooms throughout the world, The limb-positioning device 10 has a single fixation point and an adjustable friction level. Therefore a surgeon or other healthcare professional can position patient limb without the aid of an assistant. In addition, the device 10 can easily be adjusted for varying weight of limbs. Further the device can easily be adapted for use in a number of configurations. Specifically there is forearm tray 62, 70, ankle strap 72, Chinese finger traps 78, and lower leg tray 80. These different surgical devices 12 allow the surgeon to do procedures on shoulders, knees, ankles, elbows, hips and wrists with a single device 10.

The device herein has a number of advantages in the operating room. For example when the limb-positioning device 10 is used in the draped configuration with a disposable patient-receiving surgical device 14 few parts need to be sterilized and the whole device need not be sterilized. Specifically only the tension adjustment knob 26 and the male portion 30 of the attachment block 28 need to be sterilized or autoclaved. The surgical device 14 with the bar 44 attached thereto is a disposable sterile unit. Therefore no large parts need to be placed in the autoclave and the cool down times are reduced. The fitted disposable drapes 52 is a generally accepted method of rendering a piece of equipment sterile. The drape is provided with burst points 58 and fenestration 60 for connection of the autoclaved parts. Further there is a lower device inventory requirement since units need not be cycled through infection control. In addition, the compact design of the device 10 fits easily into a drawer for storage in over-crowded operating rooms As discussed above, preferably the patient-receiving surgical devices 14 are disposable. This reduces the chance of patient burn on an autoclaved device that has not cooled sufficiently. Disposable devices allow for a quick turn-around between procedures. Further the disposable devices reduce the chance of contamination.

It will be appreciated by those skilled in the art that the device herein was described using a drape 52 and a disposable patient-receiving surgical device 14. However, it would also be manufactured so that the device 10 is autoclavable and the surgical devices 14 are autoclavable. This will be advantageous in jurisdictions that have sereve restrictions regarding waste disposal. Further, although the device is described for use in the operating room it could also be used in other therapeutic settings.

It will be appreciated that the above description related to the invention by way of example only. Many variations on the invention will be obvious to those skilled in the art and such obvious variations are within the scope of the invention as described herein whether or not expressly described.

What is claimed as the invention is:

1. A limb-positioning device adapted for use in an operating room and attachable to an operating room table comprising:

a full motion arm having a plurality of pivotally connected arms with a plurality of joints therebetween, one end of the full motion arm being adapted to be attached to the operating room table;

a patient-receiving surgical device attached to a block joint at the distal end of the full motion arm; and a tension means for controlling the tension of each joint.

2. A limb-positioning device as claimed in claim 1 wherein the tension means concurrently controls the tension of all of the joints.

3. A limb-positioning device as claimed in claim 2 wherein the tension means includes a variable tension control whereby rotating a handle in one direction increases the tension on the joints and rotating the handle in the opposite direction decreases the tension.

4. A limb-positioning device as claimed in claim 3 wherein the handle is detachable.

5. A limb-positioning device as claimed in claim 4 wherein the patient-receiving surgical device is detachable.

6. A limb-positioning device as claimed in claim 5 wherein the full motion arm includes a connection arm having an attachment arm connected at one end thereof and a distal arm connected at the other end thereof and wherein a ball joint is connected between the connection arm and the attachment arm and a central joint is connected between the connection arm and the distal arm, and the block joint is a ball joint.

7. A limb-positioning device as claimed in claim 6 further including a drape having a knob fenestration and a burst point whereby the drape covers the full motion arm and both the handle and the patient-receiving surgical device are attached to the full motion arm after the drape has been placed thereon.

8. A limb-positioning device as claimed in claim 7 further including an attachment block having a male portion and a releasably attachable female portion and wherein one of the male portion and the female portion is attached to the block joint and the other of the male portion and the female portion has one of a receiving channel and a bar formed therein the receiving channel is adapted to receive the bar and the other of the receiving channel and the bar is attached to the patient-receiving surgical device.

9. A limb-positioning device as claimed in claim 8 wherein the patient-receiving surgical device is a forearm tray.

10. A limb-positioning device as claimed in claim 8 wherein the patient-receiving surgical device is a lower leg tray.

11. A limb-positioning device as claimed in claim 8 wherein the patient-receiving surgical device is a distraction harness.

12. A limb-positioning device as claimed in claim 8 wherein the patient-receiving surgical device is Chinese finger trap assembly.

13. A limb-positioning device as claimed in claim 3 wherein the patient-receiving surgical device is detachable.

14. A limb-positioning device as claimed in claim 3 wherein the patient-receiving surgical device is a forearm tray.

15. A limb-positioning device as claimed in claim 3 wherein the patient-receiving surgical device is a lower leg tray.

16. A limb-positioning device as claimed in claim 3 wherein the patient-receiving surgical device is a distraction harness.

17. A limb-positioning device as claimed in claim 3 wherein the patient-receiving surgical device is Chinese finger trap assembly.

18. A method according to claim 3 wherein the patient-receiving surgical device is Chinese finger trap assembly and the portion of the patient's anatomy is the fingers.

19. A method for positioning a portion of a patient's anatomy comprising the steps of:

providing a limb-positioning device comprising a full motion arm having a plurality of pivotally connected arms with a plurality of joints therebetween and one end of the full motion arm being adapted to be attached to an operating room table, a patient-receiving surgical device attached to a block joint at the distal end of the full motion arm, and a tension means for controlling the tension of each joint;

attaching the limb-positioning device to an operating room table;

adjusting the tension means;

securing the portion of the patient's anatomy on the patient-receiving surgical device;

positioning the patient-receiving surgical device; and tightening the tension means.

20. A method according to claim 19 wherein the patient-receiving surgical device is a forearm tray and the portion of the patient's anatomy is a forearm.

21. A method according to claim 19 wherein the patient-receiving surgical device is a lower leg tray and the portion of the patient's anatomy is a lower leg.

22. A method according to claim 19 wherein the patient-receiving surgical device is a distraction harness and the portion of the patient's anatomy is an ankle.

* * * * *